United States Patent [19]

Martinoli et al.

[11] Patent Number: 4,918,984
[45] Date of Patent: Apr. 24, 1990

[54] DEVICE FOR MEASURING THE MODIFICATION TIME OF THE PHYSICAL STATE OF A FLUID MEDIUM

[75] Inventors: Jean-Luc Martinoli, Villeneuve La Garenne; Alain Rousseau, both of Paris; Pascal Vilain, Hadancourt le Haut Clocher, all of France

[73] Assignee: Serbio, France

[21] Appl. No.: 292,171

[22] Filed: Dec. 30, 1988

[30] Foreign Application Priority Data

Dec. 30, 1987 [FR] France ............................ 87 18348
Jul. 6, 1988 [FR] France ............................ 88 09151

[51] Int. Cl.$^5$ .......................................... G01N 11/10
[52] U.S. Cl. ........................................ 73/64.1; 73/57
[58] Field of Search ................. 73/64.1, 53, 54, 57; 422/73; 436/69

[56] References Cited

U.S. PATENT DOCUMENTS

| | | | |
|---|---|---|---|
| 2,957,338 | 10/1960 | Kennedy et al. | 73/57 |
| 3,073,150 | 1/1963 | Fann | 73/54 |
| 3,967,934 | 7/1976 | Seitz et al. | 73/64.1 |
| 4,081,242 | 3/1978 | Girolami | 73/64.1 |
| 4,728,500 | 3/1988 | Higo | 422/73 |

Primary Examiner—Hezron E. Williams
Attorney, Agent, or Firm—William A. Drucker

[57] ABSTRACT

The invention relates to a method and device for determining the time of modification of the physical state of a fluid medium of the kind in which a ferromagnetic ball is placed in the bottom of a cup containing the fluid to be studied and driven with a periodic movement under the effect of an external magnetic field and in which the modifications of the movements of this ball, due to the modification, are detected. The method is characterized by the fact that the ball always follows at each period the same imposed path and in that the amplitude variations and/or the frequency of its movement are detected.

10 Claims, 3 Drawing Sheets

DEVICE FOR MEASURING THE MODIFICATION TIME OF THE PHYSICAL STATE OF A FLUID MEDIUM

BACKGROUND OF THE INVENTION

1. Field of the Invention

The present invention relates to a method of determining the time of modification of the physical state of a fluid medium and, in particular, determining the coagulation time of blood, of the kind in which a ferromagnetic ball is placed in the bottom of a cup containing the fluid to be studied and driven with a periodic movement under the effect of an external magnetic field, and in which the modifications of the movements of this ball due to the modification of the physical state are detected. The invention also relates to a device for implementing this method.

2. Description of the Prior Art

Such a method is described more particularly in the European patent n° 90 192 in which the ball thus driven moves freely over the flat and horizontal bottom of a cup. When the modification of the physical state of the fluid which is contained in the cup, and which is here blood plasma to which reagents have been added, occurs, the ball moves over a curve directed towards the inside because, so it seems, of the increase of mechanical resistance opposed by the contents of the cup, and its radial movement is detected by means well known in themselves.

The accuracy of measurements thus made leaves much room for improvement, since the radial movement of a ball towards the center of a cup of very small size is a physical magnitude which is difficult to detect and to evaluate satisfactorily. Furthermore, the reproducibility of such measurements is not good, because, particularly, of the complexity of the phenomena on which they are based.

SUMMARY OF THE INVENTION

Thus, an object of the present invention is to provide a method for measuring the modification time of the physical state of a fluid medium of the above kind which overcomes the drawbacks of known devices and, in particular, which allows measurements to be made whose accuracy, reliability and reproducibility are superior to those obtained up to now with apparatus of this type.

Furthermore, an object of the invention is a device for implementing such a method which is practically automatic and in which human intervention is reduced to a strict minimum, without its cost being prohibitive for all that.

The objective thus defined as well as others which will be clear further on are attained in accordance with the invention by a method of the above defined kind which is characterized by the fact that the ferromagnetic ball always follows the same imposed path during each period and the variation of the amplitude and/or of the frequency of this movement are detected.

When the fluid to be studied undergoes a modification of its physical state which increases its viscosity and, for example, when it coagulates if it is a question of blood plasma to which appropriate reagents have been added, the ball is braked in its movement, then stopped, so that the amplitude of its periodic movements decreases suddenly. This decrease of amplitude is detected and serves for determining the moment when the modification took place.

It will be understood that the fact that the ball, at each period, follows an imposed path which is always identical leads to high accuracy and good reproducibility of the measurements, since it is sufficient to detect the variations of a period and so of an electric frequency, or an amplitude, and so of the value of an electric signal, which is an easy operation for specialists in the field. Furthermore, such detection is obviously easier and less subject to errors than that which consists in detecting the escapement towards the center of a ball of very small size.

Advantageously, the movement of the ball is an oscillatory movement in a vertical plane. Such movement of the ball in a well defined plane, and no longer substantially haphazardly, over the flat bottom of a cup as in the above European patent, further increases the accuracy of the measurements.

Preferably, the frequency and/or the intensity of the external magnetic field which controls this oscillatory movement is adjustable.

The frequency of this field is advantageously close to the natural oscillation frequency of the ball and adjustment of its intensity causes variation of the forces of agitation created by this ball in the fluid to be studied.

Preferably, determination of the time of modification of the physical state, mentioned above, is associated with a densitometric measurement. The association of these two apparatus in the same unit appreciably simplifies a number of operations. It further makes it possible to reduce the cost because different associated members can be used for two different purposes, such as the temperature regulation devices, the feed devices and/or a part at least of the man/machine interfaces, these elements being further, if required, common to several measurement cups housed in the same apparatus.

Moreover, such association of an optical density measurement and determination of the modification time of the physical state finds its true worth if in a particularly advantageous embodiment of the present invention, the light beam used for the first of these measurements meets the path of the ball specified hereafter and serves for the second. In fact, the oscillations of the ball result in variations of illumination of the densitometric detector which are readily used for determining the amplitude of these oscillations.

Thus, the same light beam and the same detector, which is for example a photodiode, may be used both for determining the modification time of the physical state and for measuring the optical density.

In so far as the device is concerned for implementing the present invention, the bottom of the cup intended to contain the ferromagnetic ball specified hereafter has advantageously a curvilinear upwardly concave travel path whose lowest point is at its center.

It will be understood that thus the ball, when it is abandoned to itself from the highest point of its travel path, accomplishes thereon the oscillatory movement of the invention. However, such movement generally dies away fairly rapidly because of the viscosity of the fluids to be studied. Thus, the device of the invention advantageously comprises two magnetic poles which are placed on each side of the above specified travel path, outside the cup, and each of which is surrounded by a magnetic coil, as well as means for periodically and alternately feeding into the latter an electric current of adjustable period and/or intensity.

Apart from its function of sustaining the movement of the ball, this arrangement also makes it possible to adjust the period and force of such movement, which is advantageous, as was mentioned above. It will be further noted that, with respect to the device of the above European patent, any rotary member is here omitted, which has evident advantages.

Furthermore, the above specified magnetic poles terminate advantageously a U shaped magnetic carcass, each leg of which is surrounded by a coil so that the magnetic circuit which has just been described is closed, which reduces the magnetic leaks to a minimum.

In an advantageous embodiment of the device of the invention, it is the variations of the amplitude of the oscillations of the ball which are detected and, preferably, by using a light beam which passes through the cup where the ball moves, and whose occultation varies as a function of the position of the ball, it is then sufficient to transform the optical signals corresponding to this occultation into electric signals, using a photodiode for example, for readily detecting the modifications of movement of the ball.

Preferably, the cup of the invention has, at the ends of its travel path, flat, transparent and substantially parallel faces. Thus, it can be used simultaneously for a densitometer, the light ray which strikes the detector thereof then passing readily through the cup without distortion or loss.

But, in connection with this point, and according to a particularly advantageous form of the invention, the curvilinear travel path provided for the ball is placed in the device so that the path thereof cuts the light beam of the densitometer and the device comprises means for translating the occultation of this beam into an electric signal. Here, the expression "cuts" means that the path of the ball is neither totally outside nor totally inside the light beam. The result is that the oscillatory movements of the ball are transformed into electric signals which may be readily used for determining the period of the oscillations of the ball and thus for measuring the time of modification of the physical state of the fluid in the cup.

Preferably, and to increase the accuracy of the measurement, the travel path of the ball is disposed in the apparatus so that this latter, when it is at the lowest point of the travel path is substantially tangential by its top to the light beam which illuminates the detector of the densitometer. The rate of occultation of this beam then varies between zero and a maximum value reached when the ball is at one of the highest points of the travel path, a maximum of 20% being largely sufficient to obtain excellent precision.

As was mentioned above, the bottom of the cup containing this ball has, in accordance with the invention, an upwardly concave curvilinear travel path whose lowest point is at its center, which distinguishes it from the cups of this kind belonging to the prior art, such as those with a flat bottom which are commercialized by the firms ISABIOLOGIE and BEHRING, and those whose bottom comprises an annular gutter and which are described in the patents FR-A-2 465 227 and FR-A-2 566 908.

Advantageously, this cup has at its upper part an orifice for introducing reagents which opens into a substantially parallelepipedic bowl which is very elongate in the direction of the travel path which its bottom provides. In other words, this bowl has two large faces very close to one another, the distance therebetween being scarcely greater than the diameter of the ball which it contains, and two small faces on each side of the travel path, spaced apart by several times this diameter.

In one embodiment of the invention, the travel path provided by the bottom of this bowl may be a cylinder portion in which a guide groove is formed for the ball.

In another embodiment, the bottom of this bowl is a concave surface to which the two large faces of the bowl are connected on each side and which is, preferably, a surface of revolution whose axis is perpendicular to the large faces in question. The ball is then brought back by its own weight to the median line of the gutter thus formed.

This surface may be cylindrical, toric, elliptic or similar, or it may have in cross section the form of an upwardly open V.

Preferably, the opposite faces of the lower bowl of the cup of the invention are not strictly parallel to each other, but slanted through an angle less than or equal to 3° with respect to the plane of symmetry of the faces concerned.

The introduction orifice of the cup of the invention may for example be cylindrical, conical or parallelepipedic but, in this latter case, its lateral faces have beads therebetween and not sharp edges, so that the reagents are not caught by capillarity on such edges.

Such cups of the invention advantageously form part of an assembly or block of several cups which are for example molded in one piece from an appropriate plastic material.

BRIEF DESCRIPTION OF THE DRAWINGS

The following description, which has no limitative character, will clearly show how the present invention can be put into practice. It should be read with reference to the accompanying drawings in which.

DESCRIPTION OF THE PREFERRED EMBODIMENTS

Figure 2:
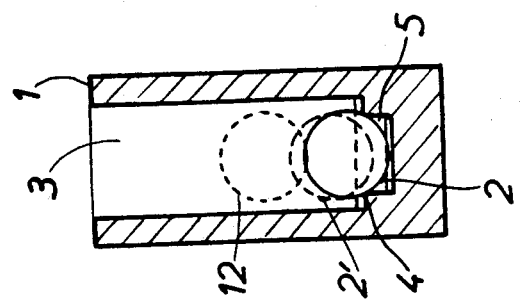
FIG. 2 is a cross sectional view through line II—II of FIG. 1.

In what follows, the apparatus of the invention will be described and its mode of operation in the case where it is a question of determining the coagulation time of a blood plasma to which the usual reagents have been added. However, it is clear that this apparatus may be used for other purposes requiring, if necessary, different modifications which are within the scope of specialists in the field.

The coagulometer shown in the figures comprises a transparent cup 1 of a general parallelepipedic shape which may be made from an adequate plastic material, which contains a ferromagnetic ball 2 and which is intended to receive the plasma to be studied to which the usual reagents have been added. More precisely, cup 1 comprises a flat cavity 3 which is extended in the transverse direction of the device and whose bottom has a travel path 4 for ball 2.

The travel path 4 extends in the vertical plane of symmetry of cup 1 in the transverse direction thereof; its profile is a circle of radius R which is centered on the vertical plane of symmetry of cup 1 so that its lowest point is situated on this axis. The result is that ball 2, when it is abandoned to itself from the highest point of the travel path 4, accomplishes thereon a pendular movement of period $T_o$ which depends on the radius of curvature R of the travel path 4. Finally, the diameter of ball 2 is slightly less than the width of cavity 3 and the travel path 4 is formed by a groove 5 in the bottom of cup 1.

On each side of the travel path 4 are placed, outside cup 1, two magnetic poles 6a and 6b which terminate a magnetic carcass 7 in the form of a U each leg of which is surrounded by a coil 8a, 8b.

The optical densitometer which is associated with this coagulometer has not been shown in detail: it comprises, on each side of cup 1, a light emitting diode 9 and a receiving photodiode 10 in front of which an optical band pass filter 11 is placed. The corresponding light beam 12 extends so as to be substantially tangential to the ball 2 when the latter is at the lowest point of its travel path 4.

In a particular embodiment given by way of non limitative example, the LED 9, whose maximum light intensity is about 480 nm, is fed from a microprocessor by a regulated current chopped at a few kilohertz, through the filter 11 which transmits the light up to about 500 nm. This diode 9 illuminates the photodiode 10 with which it is placed in line, so that the light beam passes through the plasma and cup 1. The information delivered by the photodiode 10 is transmitted to the microprocessor through a filter which causes only the chopped signal from source 9 to be held back.

Moreover, as was mentioned above, cup 1 is preferably disposed in the device so that the light beam 12 of the densitometer is substantially tangential to ball 2 when it is at the lowest point of the travel path 4.

The operating mode of this device is as follows. The plasma to be studied to which the usual reagents have been added is poured into cup 1 up to a level such that it cuts the light beam 12.

A current is fed alternately into coils 8a and 8b so that ball 2 executes on its travel path 4 a pendular movement of period T close to its natural oscillation period. When the blood coagulates, the amplitude of its oscillations decreases suddenly and determination of the moment when this phenomenon occurs makes possible that of the coagulation time. As for determining the moment when the periodic movement of ball 2 stops, it will be recalled that the light beam 12 of the densitometer is substantially tangential to this ball when it is at the lowest point of its travel path 4. The result is that it partially occults the light beam 12 when it moves away therefrom, the maximum occultation taking place of course when ball 2 reaches it highest point where it is shown with broken lines at 2'. It is sufficient for 20% of the surface of light beam 12 to be occulted when ball 2 is at its highest point so that excellent precision is obtained for the measurements.

It will be understood that it is sufficient to insert an appropriate electric circuit at the output of the receiving photodiode 10 for detecting stopping of ball 2 when the plasma contained in cup 1 coagulates. Such a circuit is within the scope of specialists in the matter and it will not be described here in greater detail.

Figure 1:
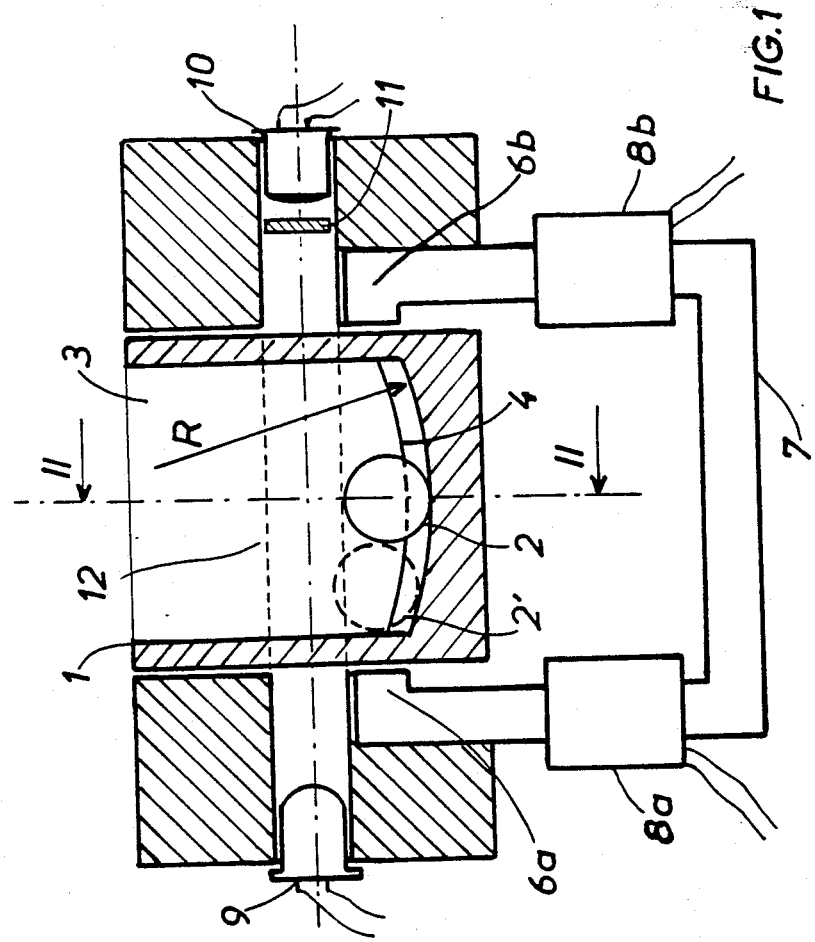
FIG. 1 shows a schematic vertical sectional view of a device for implementing the method of the present invention.

Variants of the cup which is shown in FIGS. 1 and 2 will now be described with reference to FIGS. 3 to 8.

Each cup 20 in FIGS. 3 to 7 forms part of an assembly or block 13 of several cups. Cup 20 has at its lower part a bowl with two opposite closely spaced side walls 21 and 22 defining with the bottom 30 a travel path for a ball 40 and two other opposite side walls 21' and 22' separated from each other by a distance greater than that separating the closely spaced walls 21 and 22.

Walls 21 and 22 are substantially parallel to each other. More precisely, they are either parallel, or slightly slanted with respect to the vertical axis of symmetry V (or plane of symmetry II) of the bowl. Similarly, walls 21' and 22' are substantially parallel to each other, i.e. they are either parallel or also slightly slanted with respect to said axis of symmetry V. Advantageously, it is preferable for walls 21 and 22, on the one hand, and 21' and 22', on the other, to be slightly slanted with respect to the axis V so that the space between these walls narrows from top to bottom of the bowl. The slant angle of these walls with respect to the vertical axis of symmetry V will be advantageously less than or equal to 3°, and preferably less than or equal to 1°.

In the case where the concave surface of bottom 30 is of revolution, its axis of revolution U is perpendicular to the vertical plane of symmetry II of the bowl. This concave surface is advantageously, as mentioned above, either cylindrical or toric.

Cup 20 has at its upper part a device 14 for introducing reagents by pipette in the form of a funnel. Advantageously, this device 14 preferably has at the level of its opening opposite side walls 41 and 42, on the one hand, and 43, 44 on the other, which are slightly slanted with respect to axis V.

It is also preferable for the connection of each pair of walls 41/42, 41/44, 42/43 and 42/44 not to be formed by too sharp an edge but for this connection to be curvilinear. In practice, it is recommended that the cup have at its upper part an introduction orifice 14 defined by opposite faces 41, 42, on the one hand, and opposite faces 43 and 44, on the other, which is substantially square or rectangular. Such an arrangement facilitates the introduction of one or more reagents by pipette whereas the presence of sharp edges would prevent the flow of the reagent(s) to the lower part of the cup by surface tension phenomena. With several curvilinear connections, the location of the different reagents to be introduced can be readily identified.

Figure 8:
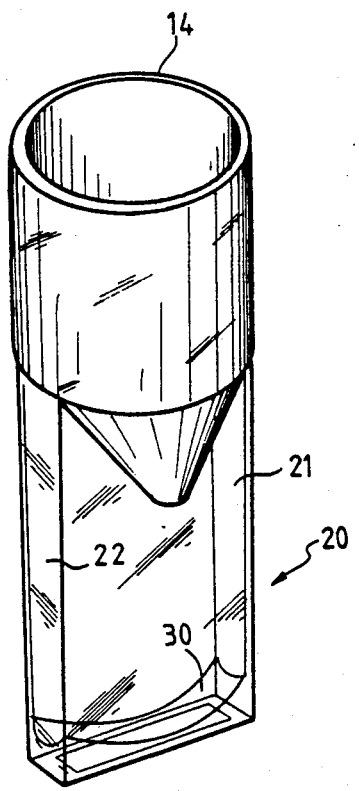
FIG. 8 a perspective view of an isolated cup of the invention.

In a variant, as shown in FIG. 8, the introduction device 14 may be cylindrical or in the form of a truncated cone.

Figure 3:
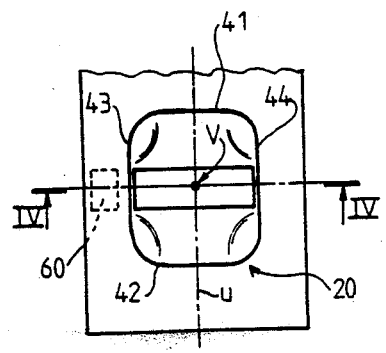
FIG. 3 is a bottom view of a cup of the invention forming part of an assembly of several cups.
Figure 4:
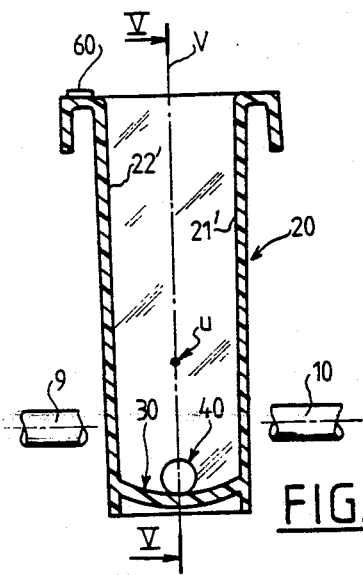
FIG. 4 is a section through IV—IV of FIG. 3.
Figure 5:
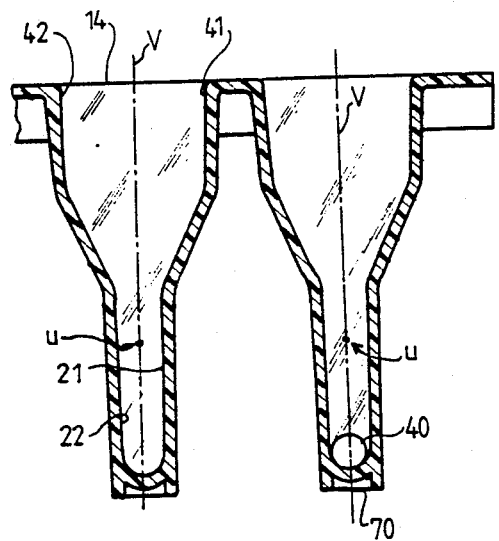
FIG. 5 is a section through V—V of FIG. 4.

The assembly 13 of cups may have at least one identification means 60 (FIGS. 3 and 4). This identification means may for example be, as shown in FIG. 6, a calendar indication such as the year, 61, a calendar indication such as the month in the year, 62, initials or monogram in relief 63 of the manufacturer of the block of cups, or else a means 64 for distinctively marking this block.

Figure 6:
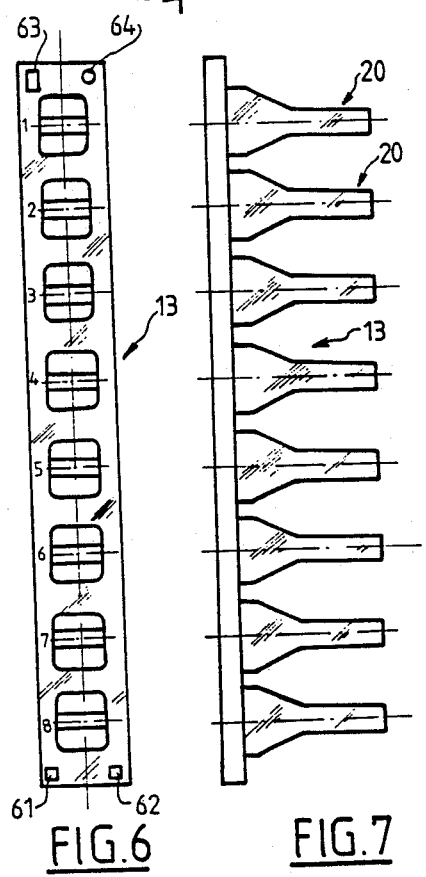
FIG. 6 is a top view of a cup assembly.
Figure 7:
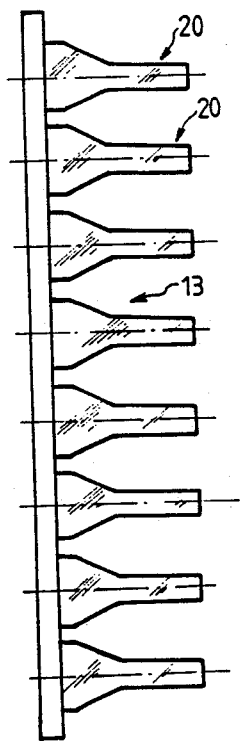
FIG. 7 is a side view of the cup assembly shown in FIG. 6.

Furthermore, the block 13 of cups may comprise indications, e.g. numbers or letters, shown by the FIGS. 1 to 8 in FIG. 6, for distinguishing each of the cups of the block.

Each cup 20 or each block 13 of cups may be made from an appropriate material, particularly from glass or better still from a plastic material. Preferably each cup or each block of cups is made from plastic material, particularly using a technique of molding by injection at the level of reference 70 of FIG. 5.

The blocks or sets 13 of cups 20 of the invention may be used in automatic and semi-automatic analyzers. When an automatic analyzer is used capable of carrying out a series of different measurements, it is preferable to use individual bowls as FIG. 1, called, the automatic analyzer being thus able to make rapid measurements on different samples depending on the urgency. In practice, commercial automatic analyzers operate generally with two pipette operations, i.e. they make possible the introduction of two different reagents; the absence of sharp edges at the upper part of cups 20 of the invention, i.e. at the level of the introduction devices 14, make it possible to carry out the two pipette operations in question efficiently.

Without departing from the scope or spirit of the present invention, it would be possible to make different modifications to the embodiment which has just been described. Thus, for example, an inductive, capacitive or optoelectronic sensor could be used instead of using the detector of the densitometer.

What is claimed is:

1. An apparatus for determining the time of change of the physical state of a fluid sample comprising:
   (i) a container for holding the fluid sample, said container having a bottom;
   (ii) a ferromagnetic member movable in the bottom of the container along a predetermined curvilinear path;
   (iii) means for generating a periodic magnetic field coupled to said ferromagnetic member, said periodic magnetic field imparting to said ferromagnetic member a sustained pendular motion along said path, said periodic magnetic field having a period substantially equalling the natural period of pendular motion of said ferromagnetic member along said path within said fluid sample and
   (iv) detecting means for detecting the variations of the amplitude and/or the frequency of said pendular motion during said time of change.

2. An apparatus as claimed in claim 1, wherein said ferromagnetic member is a ball, said container has a vertical plane of symmetry and said predetermined path is contained in said vertical plane of symmetry.

3. An apparatus as claimed in claim 1, said apparatus further comprising means for adjusting the period and/or the intensity of said periodic magnetic field.

4. An apparatus as claimed in claim 2, wherein said path is upwardly concave with its lowest point at the center thereof.

5. An apparatus as claimed in claim 2, wherein said path is defined by a groove formed in said bottom and shaped as a segment of a circle.

6. An apparatus as claimed in claim 4, wherein said container is transparent and said apparatus further comprises densitometer means including a light source producing a light beam across said container and photosensitive means receiving said light beam for generating densitometric signals, said light source and photosensitive means being so positioned in said vertical plane of symmetry relative to said predetermined path that said light beam is substantially tangential to said ball when said ball is located at the lowest point of said path and said detecting means including said photosensitive means.

7. An apparatus as claimed in claim 2, wherein said container has a substantially parallelepipedic lower portion closed by said bottom, said lower portion having two smaller sides and two larger sides, said larger sides being substantially parallel to said plane of symmetry and located at a distance from each other which does not substantially exceed the diameter of said ball.

8. An apparatus as claimed in claim 7, wherein said parallelepipedic portion has an axis of symmetry, both said smaller and said larger sides being slanted through an angle not exceeding 3° with respect to said axis of symmetry.

9. An apparatus as claimed in claim 7, wherein said bottom is shaped as a surface of revolution having an axis at right angles with said plane of symmetry.

10. An apparatus as claimed in claim 2, wherein said container further has a substantially parallelepipedic upper portion forming an opening for introduction of reagents in the fluid sample and said upper portion has side walls having inner faces connected together by beads.

* * * * *